: US010258968B2

United States Patent
Buelow et al.

(10) Patent No.: US 10,258,968 B2
(45) Date of Patent: *Apr. 16, 2019

(54) CATALYST COATINGS INCORPORATING BINDER COMPOSITIONS

(71) Applicant: BASF Corporation, Florham Park, NJ (US)

(72) Inventors: Mark Thomas Buelow, Flemington, NJ (US); Steven W. Chin, Port Reading, NJ (US); Jeffrey Barmont Hoke, North Brunswick, NJ (US); Nicholas R. Leclerc, Hillsborough, NJ (US); David M. Robinson, Princeton, NJ (US)

(73) Assignee: BASF Corporation, Florham Park, NJ (US)

( * ) Notice: Subject to any disclaimer, the term of this patent is extended or adjusted under 35 U.S.C. 154(b) by 409 days.

This patent is subject to a terminal disclaimer.

(21) Appl. No.: 14/528,280

(22) Filed: Oct. 30, 2014

(65) Prior Publication Data

US 2015/0119235 A1 Apr. 30, 2015

Related U.S. Application Data

(60) Provisional application No. 61/897,557, filed on Oct. 30, 2013.

(51) Int. Cl.
*B01J 21/04* (2006.01)
*B01J 21/08* (2006.01)
(Continued)

(52) U.S. Cl.
CPC ............... *B01J 23/75* (2013.01); *A61L 9/00* (2013.01); *B01D 53/8675* (2013.01); *B01D 53/88* (2013.01); *B01J 23/34* (2013.01); *B01J 31/28* (2013.01); *B01J 31/32* (2013.01); *B01J 35/1019* (2013.01); *B01J 35/1042* (2013.01); *B01J 35/1047* (2013.01); *B01J 35/1061* (2013.01); *B01J 37/0215* (2013.01); *B01D 2255/2073* (2013.01); *B01D 2255/2092* (2013.01); *B01D 2255/20746* (2013.01);
(Continued)

(58) Field of Classification Search
CPC ......... B01J 23/34; B01J 31/08; B01J 37/0201
See application file for complete search history.

(56) References Cited

U.S. PATENT DOCUMENTS 4,123,391 A 10/1978 Noguchi et al.
4,822,589 A 4/1989 Kiyoura et al.
(Continued)

FOREIGN PATENT DOCUMENTS

CN 1812835 8/2006
EP 0275620 7/1988
(Continued)

OTHER PUBLICATIONS

Mold Materials (106 Glass Transition Temperature Tg of Plastics, MiSUMi Technical Tutorial, Dec. 2011).*
(Continued)

*Primary Examiner* — Jun Li
(74) *Attorney, Agent, or Firm* — Lowenstein Sandler LLP

(57) ABSTRACT

Disclosed in certain implementations is a catalysis composition that includes a metal catalyst and a support material impregnated with the metal catalyst.

26 Claims, 8 Drawing Sheets

(51) Int. Cl.
*B01J 21/12* (2006.01)
*B01J 31/32* (2006.01)
*B01J 23/75* (2006.01)
*B01J 23/34* (2006.01)
*B01D 53/86* (2006.01)
*A61L 9/00* (2006.01)
*B01J 31/28* (2006.01)
*B01D 53/88* (2006.01)
*B01J 35/10* (2006.01)
*B01J 37/02* (2006.01)
*B01J 35/00* (2006.01)

(52) U.S. Cl.
CPC ...... *B01D 2255/30* (2013.01); *B01D 2255/92* (2013.01); *B01D 2257/106* (2013.01); *B01D 2257/404* (2013.01); *B01D 2257/502* (2013.01); *B01D 2257/702* (2013.01); *B01D 2257/708* (2013.01); *B01D 2259/4566* (2013.01); *B01J 35/002* (2013.01); *B01J 37/0201* (2013.01); *B01J 37/0203* (2013.01); *B01J 37/0219* (2013.01); *B01J 2231/62* (2013.01)

(56) References Cited

U.S. PATENT DOCUMENTS

| | | | |
|---|---|---|---|
| 5,422,331 A | 6/1995 | Galligan et al. | |
| 5,948,419 A | 9/1999 | Bankert et al. | |
| 6,156,283 A * | 12/2000 | Allen | B01D 53/864 423/210 |
| 6,506,493 B1 | 1/2003 | Kumar et al. | |
| 6,517,899 B1 | 2/2003 | Hoke et al. | |
| 6,555,079 B2 | 4/2003 | Hoke et al. | |
| 8,450,235 B2 | 5/2013 | Suzuki et al. | |
| 2003/0202916 A1 | 10/2003 | Liu et al. | |
| 2005/0100492 A1 | 5/2005 | Hoke et al. | |
| 2007/0060472 A1 | 3/2007 | Fisher et al. | |
| 2007/0163332 A1 | 7/2007 | Tsujii et al. | |
| 2007/0203022 A1 | 8/2007 | Schlogl et al. | |
| 2009/0035208 A1 | 5/2009 | Axmann et al. | |
| 2010/0021360 A1 | 1/2010 | Leenders | |
| 2010/0158775 A1 | 6/2010 | Galligan et al. | |
| 2010/0158780 A1 | 6/2010 | Galligan et al. | |
| 2011/0065839 A1 | 3/2011 | Ayambem et al. | |
| 2011/0177251 A1 * | 7/2011 | Boyd | C03C 17/005 427/389.7 |
| 2012/0322653 A1 | 12/2012 | Johnson et al. | |

FOREIGN PATENT DOCUMENTS

| | | | |
|---|---|---|---|
| JP | 2011032257 | 2/2011 | |
| WO | WO 9622146 A2 * | 7/1996 | ............ B01D 53/02 |
| WO | 2004096435 | 11/2004 | |
| WO | 2014/023955 | 2/2014 | |

OTHER PUBLICATIONS

Rezaei et al., "Low temperature oxidation of toluene by ozone ober MnOx/u-alumina and MnOx/MCM-41 catalysts," Chemical Engineering Journal 198-199, pp. 482-490, Aug. 2012.
Kapteijn et al., "Alumina-Supported Manganese Oxide Catalysts: I. Characterization: Effect of Precursor and Loading," Journal of Catalysis 150(1), pp. 94-104, Nov. 1994.
Wu et al., "Clean-air catalyst system for on-road applications: I. Evaluation of potential catalysts," Applied Catalysis B: Environmental 18(1-2), pp. 79-91, Sep. 1998.
Gandia et al.; Preparation and characterization of manganese oxide catalysts supported on Alumina and zirconia-pillared clays; Applied Catalysis A: general vol. 196 pp. 281-292 (2000) Abstract, p. 283, col. 1 para 3; p. 287, col. 1 para 1.
Notification of Transmittal of the International Search Report and the Written Opinion of the International Searching Authority, or the Declaration for International Application No. PCT/US 14/63062, filed Oct. 30, 2014, dated Jun. 5, 2015, 15 pages.
Kirk, et al., "Catalysis," Kirk-Othmer Encyclopedia of Chemical Technology, 4th ed., vol. 5, p. 171, Dec. 1998.
Extended European Search Report dated Jul. 5, 2017 in corresponding EP App. 14858531.8, 6 pages.
Singoredjo, et al., "Alumina Supported Manganese Oxides for the Low-Temperature Selective Catalytic Reduction of Nitric Oxide with Ammonia", Applied Catalysis B: Environmental 1(4), pp. 297-316, Dec. 1992.
Liu, Fudong et al., "Effect of Manganese Substitution on the Structure and Activity of Iron Titanate Catalyst for the Selective Catalytic Reduction of NO with NH3.", Applied Catalysis B: Environmental, vol. 93, pp. 194-204, 2009, 11 pages.

* cited by examiner

CATALYST COATINGS INCORPORATING BINDER COMPOSITIONS

CROSS REFERENCE TO RELATED APPLICATION

This application claims the benefit of priority of U.S. Provisional Patent Application No. 61/897,557, filed Oct. 30, 2013, which is hereby incorporated by reference herein in its entirety.

FIELD OF THE INVENTION

The present invention relates to a method and apparatus for cleaning the atmosphere. More particularly, the invention relates to a substrate such as a motor vehicle radiator including pollution treating composition layered thereon.

BACKGROUND OF THE INVENTION

Atmospheric pollution is a concern of increasing importance as the levels of various atmospheric pollutants continue to increase. One primary pollutant of concern is ozone.

Ozone is a molecule that consists of three oxygen atoms. Naturally-occurring ozone is formed miles above the earth in the stratosphere. This ozone layer is responsible for absorbing the majority of the sun's harmful ultraviolet radiation. Unfortunately, the ozone at ground level is a health risk and the major component of smog. This ground level ozone is the cause of many adverse effects, such as irritation of and damage to a subject's lungs, eyes, nose and throat. Ground level ozone is produced by the reactions of nitrogen oxides and volatile organic compounds in the presence of direct sunlight. The main sources of nitrogen oxide and volatile organic compound gases are mobile emissions, industrial factories, electrical plants, chemical solvents, and gasoline vapors.

Typical pollution control measures are directed toward removing nitrogen oxides and volatile organic compounds at emission sources. Pollution control is also performed by direct treatment of ozone at ground level utilizing vehicle heat exchangers. In these processes, ozone in the air that passes over catalyst coated surfaces, such as radiators, convert ozone molecules into oxygen molecules. These processes capitalize on the large volume of air that passes through a vehicle's radiator.

There continues to be a need in the art for methods and compositions for effectively treating ground level pollution. These methods and compositions should exhibit long term performance and efficient manufacturing operations.

SUMMARY

It is an object of certain implementations of the disclosure to provide a catalyst composition to treat pollutants in the atmosphere.

It is an object of certain implementations of the disclosure to provide a substrate including a catalyst composition to treat pollutants in the atmosphere.

It is an object of certain implementations of the disclosure to provide a heat exchanger including a catalyst composition to treat pollutants in the atmosphere.

It is an object of certain implementations of the disclosure to provide an automobile radiator including a catalyst composition to treat pollutants in the atmosphere.

It is an object of certain implementations of the disclosure to provide a method of preparing a catalyst composition to treat pollutants in the atmosphere.

It is an object of certain implementations of the disclosure to provide a method of preparing a substrate including a catalyst composition to treat pollutants in the atmosphere.

It is an object of certain implementations of the disclosure to provide a method of preparing a heat exchanger including a catalyst composition to treat pollutants in the atmosphere.

It is an object of certain implementations of the disclosure to provide a method of preparing an automobile radiator including a catalyst composition to treat pollutants in the atmosphere.

The above objects and others are met by the present disclosure, which in certain implementations is directed to a catalysis composition including a metal catalyst and a support material impregnated with the metal catalyst. In certain implementations, the catalyst composition has a deactivation factor of at least 0.5.

In certain implementations, the disclosure is directed to a catalysis composition including a metal catalyst and a support material including surface hydroxyl groups, wherein the metal catalyst is impregnated in the support material in an amount of about 0.5 atoms to about 2.5 atoms per surface hydroxyl group.

In certain implementations, the disclosure is directed to a catalysis composition including a metal catalyst and a support material, wherein the metal catalyst is impregnated in the support material in an amount ranging from about 10% to about 20% metal atoms by mass (e.g., mass percent of overall catalysis composition).

In certain implementations, the disclosure is directed to a catalysis composition including a metal catalyst and a support material, wherein the metal catalyst is impregnated in the support material in an amount ranging from about 10% to about 25% metal atoms by mass.

In certain implementations, the disclosure is directed to a catalysis composition including a metal catalyst and a support material, wherein the metal catalyst is impregnated in the support material in an amount ranging from about 5% to about 30% metal atoms by mass.

In certain implementations, the disclosure is directed to a catalysis composition including a metal catalyst and a support material, wherein the metal catalyst is impregnated in the support material in an amount ranging from about 12% to about 18% metal atoms by mass.

In certain implementations, the disclosure is directed to a catalysis device including an automobile radiator and an ozone catalyst coating at least partially layered on the radiator, the catalyst coating including a metal catalyst and a support material impregnated with the ozone catalyst. In certain implementations, the coating has a deactivation factor of at least 0.5.

In certain implementations, the disclosure is directed to a catalysis device consisting essentially of an automobile radiator and an ozone catalyst coating at least partially layered on the radiator, wherein the catalyst coating including a metal catalyst and a support material impregnated with the ozone catalyst. In certain implementations, the catalyst coating has a deactivation factor of at least 0.5.

In certain implementations, the disclosure is directed to a catalysis device including an automobile radiator and a manganese oxide catalyst coating (e.g., derived from manganese acetate) at least partially layered on the radiator, wherein the catalyst coating including the manganese oxide catalyst (e.g., derived from manganese acetate), a support material impregnated with the metal catalyst, wherein the metal catalyst is impregnated in the support material in an amount ranging from about 12% to about 18% metal atoms by mass.

In certain implementations, the disclosure is directed to a catalysis device consisting essentially of an automobile radiator and a manganese oxide catalyst coating (e.g., derived from manganese acetate) at least partially layered on the radiator, wherein the catalyst coating including the manganese oxide catalyst (e.g., derived from manganese acetate), a support material impregnated with the metal catalyst, wherein the metal catalyst is impregnated in the support material in an amount ranging from about 12% to about 18% metal atoms by mass.

In certain implementations, the disclosure is directed to a method of preparing a catalyst composition including mixing particulate support material in a solution of a metal catalyst to obtain a deactivation factor of the composition of at least 0.5.

In certain implementations, the disclosure is directed to a method of preparing a catalysis device including at least partially layering an ozone catalyst coating on an automobile radiator, wherein the catalyst coating including an ozone catalyst and a support material impregnated with the catalyst and the catalyst has a deactivation factor of at least 0.5.

In certain implementations, the disclosure is directed to a method of preparing a catalysis device including at least partially layering an ozone catalyst coating on an automobile radiator, wherein the catalyst coating including an ozone catalyst, a support material impregnated with the catalyst, the catalyst has a deactivation factor of at least 0.5 and the radiator does not include an additional catalyst layer or support layer.

In certain implementations, the disclosure is directed to a method of preparing a catalyst composition including mixing particulate support material in a solution of a metal catalyst wherein the catalyst is impregnated in the support material in an amount ranging from about 10% to about 20% metal atoms by mass.

In certain implementations, the disclosure is directed to a method of preparing a catalysis device including at least partially layering a manganese oxide catalyst coating (e.g., derived from manganese acetate) on an automobile radiator, wherein the catalyst coating including a metal catalyst and a support material impregnated with the catalyst and the catalyst has a deactivation factor of at least 0.5.

In certain implementations, the disclosure is directed to a method of preparing a catalysis device including at least partially layering a manganese oxide catalyst coating (e.g., derived from manganese acetate) on an automobile radiator, wherein the catalyst coating including a metal catalyst, a support material impregnated with the catalyst, the radiator does not include an additional catalyst layer or support layer and the catalyst has a deactivation factor of at least 0.5.

In certain implementations, the disclosure is directed to a method of cleaning the atmosphere including contacting a composition as disclosed herein with an airstream including a pollutant and catalyzing the pollutant to a less toxic compound.

In certain implementations, the disclosure is directed to a method of cleaning the atmosphere including contacting a device as disclosed herein with an airstream including a pollutant and catalyzing the pollutant to a less toxic compound.

In certain implementations, the disclosure is directed to a method of cleaning the atmosphere including operating an automobile including a device as disclosed herein.

In certain implementations, the disclosure is directed to an automobile including a device as disclosed herein.

In certain implementations, the disclosure is directed to an automobile part including a composition as disclosed herein.

In certain implementations, a catalysis composition includes a metal oxide catalyst and a support material impregnated with the metal oxide catalyst. The metal oxide catalyst is impregnated in the support material such that at least about 15% of a total number of metal atoms in the metal oxide catalyst are detectable by surface x-ray photoelectron spectroscopy.

In certain implementations, a method includes providing a slurry of a catalysis composition, the catalyst composition including a metal oxide catalyst and a support material impregnated with the metal oxide catalyst. The metal oxide catalyst is impregnated in the support material such that at least about 15% of a total number of metal atoms in the metal oxide catalyst are detectable by surface x-ray photoelectron spectroscopy. The method further includes coating the slurry onto a substrate to produce a catalyst layer.

In certain implementations, a catalysis composition includes a metal oxide catalyst and a support material impregnated with the metal oxide catalyst such that a cumulative pore volume of the catalysis composition is at least about 0.70 mL/g.

In certain implementations, a method includes providing a slurry of a catalysis composition, the catalysis composition including a metal oxide catalyst a support material impregnated with the metal oxide catalyst such that a cumulative pore volume of the catalysis composition is at least about 0.70 mL/g. The method further includes coating the slurry onto a substrate to produce a catalyst layer.

In certain implementations, a catalysis composition includes a metal oxide catalyst and a support material impregnated with the metal oxide catalyst such that an x-ray diffraction spectrum of the catalysis composition includes at least one characteristic peak including at least one of a manganosite peak, pyrolusite peak, a bixbyite peak, or a hausmannite peak.

In certain implementations, a method includes providing a slurry of a catalysis composition, the catalysis composition including a metal oxide catalyst and a support material impregnated with the metal oxide catalyst such that an x-ray diffraction spectrum of the catalysis composition includes at least one characteristic peak including at least one of a manganosite peak, pyrolusite peak, a bixbyite peak, or a hausmannite peak. The method further includes coating the slurry onto a substrate to produce a catalyst layer.

In certain implementations, a catalysis composition includes a metal oxide catalyst and a support material impregnated with the metal oxide catalyst such that the catalysis composition, when coated onto a substrate and contacted with an airstream having an initial ozone concentration, is adapted to convert ozone within the airstream such that a final ozone concentration of the airstream is reduced by greater than 30% of the initial ozone concentration after the catalysis composition is contacted with the airstream.

In certain implementations, a method includes contacting a catalyst layer with an airstream. The catalyst layer includes a support material impregnated with a manganese oxide catalyst. The airstream has an initial ozone concentration prior to contacting the catalyst layer, and the airstream has a final ozone concentration after contact the catalyst layer, the final ozone concentration being reduced by greater than 30% of the initial ozone concentration.

In certain implementations, a catalysis composition includes a metal oxide catalyst and a support material impregnated with the metal oxide catalyst. The catalyst composition further includes a first binder and a second binder such that, after coating the catalysis composition onto a substrate, an ultrasonic washcoat adhesion weight loss of the substrate is less than 1.60%.

In certain implementations, a method includes providing a slurry of a catalysis composition, the catalysis composition including a metal oxide catalyst, a support material impregnated with the metal oxide catalyst, a first binder, and a second binder. The method further includes coating the slurry onto a substrate to produce a catalyst layer. After coating the catalysis composition onto the substrate, an ultrasonic washcoat adhesion weight loss of the substrate is less than 1.60%.

In certain implementations, the catalysis composition further includes particles, wherein the particles include one or more of aluminum particles, graphite particles, silicon carbide particles, or sapphire particles. In certain implementations, the particles are in a form of flakes. In certain implementations, an average size of the particles ranges from about 1 micrometer to about 30 micrometers. In certain implementations, an average size of the particles ranges from about 1 micrometer to about 10 micrometers.

In certain implementations, a catalysis device includes an automobile component and any of the aforementioned catalysis compositions (or implementations thereof described herein) coated onto the automobile component.

The term "atmosphere" is defined herein as the mass of air surrounding the earth. The term "ambient air" shall mean the atmosphere which is drawn or forced towards the outer surface of a composition or device as disclosed herein.

The term "automobile" means any wheeled or unwheeled motorized machine or vehicle for (i) transporting of passengers or cargo or (ii) performing tasks such as construction or excavation moving. Vehicles can have, e.g., at least 2 wheels (e.g., a motorcycle or motorized scooter), at least 3 wheels (e.g., an all-terrain vehicle), at least 4 wheels (e.g., a passenger automobile), at least 6 wheels, at least 8 wheels, at least 10 wheels, at least 12 wheels, at least 14 wheels, at least 16 wheels or at least 18 wheels. The vehicle can be, e.g., a bus, refuse vehicle, freight truck, construction vehicle, heavy equipment, military vehicle or tractor. The vehicle can also be a train, aircraft, watercraft, submarine or spacecraft.

The term "radiator" means an apparatus to effect cooling to an associated device through heat exchange.

The term "aged % conversion" means the percent conversion after a time relative to the useful life of the device (e.g., exposure to the equivalent of 150,000 miles of on-road driving for an automobile component).

The term "deactivation factor" means the ratio of the aged % conversion of a pollutant (e.g., ozone to oxygen) by a composition or device of the present invention to the fresh % conversion measured at conditions of 800,000 $hr^{-1}$ space velocity and 75° C. In certain implementations, the deactivation factor is calculated based on an ozone catalysis composition as disclosed herein coated on an automobile radiator. The radiator may have, e.g., a 26 mm depth and 49 cells per square-inch (cpsi) or may have a 16 mm depth and 63 cpsi. In other implementations, the radiator may include a frame forming a window, a plurality of tubular conduits within the window for carrying a coolant and fins between the conduits having louvers formed therein.

BRIEF DESCRIPTION OF THE DRAWINGS

The above and other features of the present disclosure, their nature, and various advantages will become more apparent upon consideration of the following detailed description, taken in conjunction with the accompanying drawings, in which.

DETAILED DESCRIPTION

Figure 1:
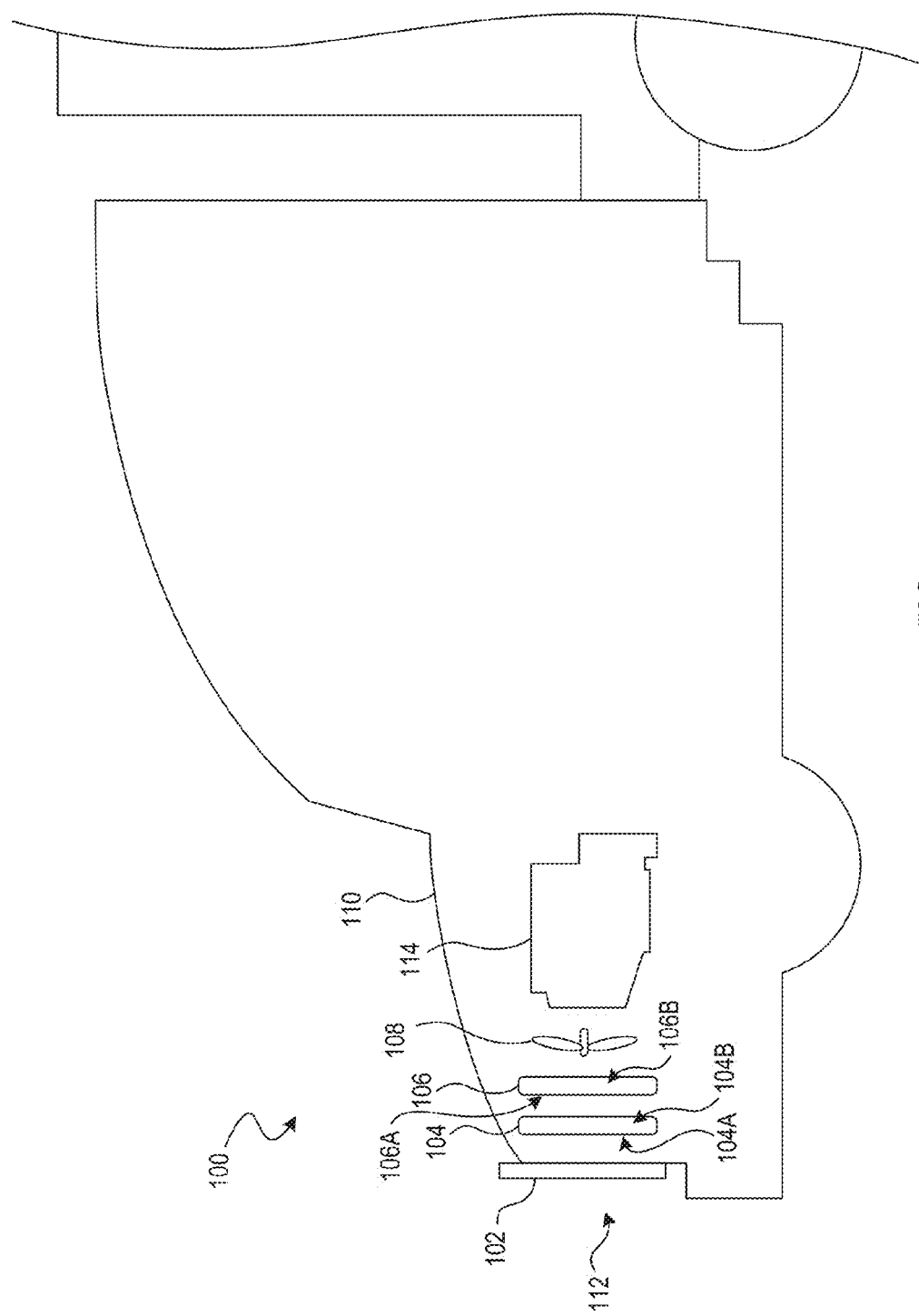
FIG. 1 is a side schematic view of a truck including components that may be coated with a catalyst layer in accordance with an implementation.

The present disclosure is directed to a compositions and methods of treating pollutants. In one implementation, the disclosure is directed to a surface treatment of a heat exchange device (e.g., an automobile radiator) so that pollutants contained in ambient air may be readily converted to less harmful compounds. The present disclosure can be adapted for the conversion of hydrocarbons, volatile organic compounds (e.g., aromatics, aldehydes, carboxylic acids, etc.), ozone and carbon monoxide into less harmful compounds such as oxygen, carbon dioxide and water vapor.

In heat exchanger implementations, the flow of ambient air there through may be treated in accordance with the present invention. In certain aspects of the disclosure, the outer surface of the heat exchange device is capable of catalytically converting pollutants to less harmful compounds without adversely affecting the heat exchange activity of the device.

In other aspects of the disclosure, the heat exchanger provides an acceptable catalytic activity that is maintained over the useful life of the device. In other aspects of the disclosure, the intended activity may be obtained with a single coat of catalytic material onto the substrate (e.g., the heat exchanger).

In certain implementations, the present disclosure is directed to a catalysis composition including a metal catalyst and a support material impregnated with the metal catalyst. In certain implementations, the deactivation factor is least 0.5.

The catalysis compositions disclosed herein may treat a pollutant, e.g., selected from the group consisting of ozone, hydrocarbons, volatile organic compounds (e.g., aromatics, aldehydes, carboxylic acids, etc.), carbon dioxide, carbon monoxide and nitrous oxides (e.g., nitric oxide and nitrogen dioxide). For example, the catalysis composition may convert ozone to oxygen; carbon dioxide to water; carbon monoxide to carbon dioxide; or nitrous oxides to nitrogen or nitrate.

The metal of the catalysis composition disclosed herein may be a base metal. The base metal may be, e.g., selected from the group consisting of iron, copper, chromium, zinc, manganese, cobalt, nickel, compounds containing the same and combinations thereof.

In other implementations, the metal of the catalysis composition as disclosed herein is a precious metal. The precious metal may be, e.g., selected from the group consisting of platinum, palladium, rhodium, ruthenium, gold, silver, compounds containing the same and combinations thereof.

In one implementation, the metal is manganese which may be derived from a manganese acetate precursor.

The support material can be a high surface area support material. In certain implementations, the surface area of the support material has a surface area of at least about 50 $m^2/g$; at least about 100 $m^2/g$; from about 50 $m^2/g$ to about 5000 $m^2/g$ or from about 100 $m^2/g$ to about 300 $m^2/g$.

The surface area of the material may be determined by the BET (Brunauer-Emmett-Teller) method according to DIN ISO 9277:2003-05. The specific surface area is determined by a multipoint BET measurement in the relative pressure range from 0.05-0.3 $p/p_0$.

In other implementations, the support material has a large pore volume. In certain implementations, the support material has an average pore volume ranging from about 0.5 mL/g to about 3 mL/g, about 0.7 mL/g to about 1.2 mL/g, about 0.8 mL/g to about 1.5 mL/g, about 0.8 mL/g to about 2 mL/g, about 0.8 mL/g to about 2 mL/g, about 1.2 mL/g to about 2 mL/g, or about 1.5 mL/g to about 2 mL/g.

The material utilized as the support material can be a refractory oxide or any other suitable material. In certain implementations, the material is metal organic framework.

For example, the support material may include, e.g., a material selected from the group consisting of ceria, lanthana, alumina, titania, silica, zirconia, carbons, metal organic framework, clay, zeolites and combinations thereof.

In one implementation, the support material is selected from the group consisting of alumina, silica and combinations thereof. The alumina and silica may be in a ratio (w/w) of about 1:99 to 99:1; about 1:50 to 50:1; about 10:1 to about 30:1 or about 19:1.

In one implementation, the support material may have surface hydroxyl groups. In such an implementation, the catalyst may be impregnated in the support material, e.g., in an amount of at least 0.5 atom per surface hydroxyl group; in an amount of at least 1.0 atom per surface hydroxyl group; in an amount of about 0.5 atom to about 2.5 atoms per surface hydroxyl group or in an amount of about 1 atom to about 1.5 atoms per surface hydroxyl group.

In another implementation, the metal component of the catalysis composition may be in an amount, e.g., ranging from about 5% to about 30% by mass, about 10% to about 25% by mass, or about 12% to about 18% by mass.

In certain implementations of the disclosure, a portion of the catalyst is in amorphous form. In certain aspects, at least 50%, at least 60%, at least 75% or at least 85% of the catalyst is in amorphous form.

The catalyst composition of the present invention may be used independent of other materials to treat the atmosphere or can be combined with other materials. In one implementation, the composition is coated onto a substrate. The substrate can be, e.g., a heat exchanger such as an automobile radiator or a battery cooling device.

In certain implementations, the catalysis composition of the present disclosure may include an acid additive. The acid additive may be an organic acid or any other suitable acid. For example, the acid may be selected from the group consisting of tartaric acid, malic acid, fumaric acid, acetic acid, citric acid and a combination thereof.

The compositions and devices of the present invention may have a deactivation factor of at least 0.5; at least 0.55, at least 0.6 at least 0.65, at least 0.7 or at least 0.8. In one implementation, the deactivation factor is measured with the catalysis composition coated onto a radiator.

In certain implementations, the deactivation factor of the device is at least 0.55, at least 0.60 or at least 0.65 based on a radiator (e.g., an automobile radiator) with 26 mm depth and 49 cpsi. In other implementations, these parameters are obtained on a radiator is fitted with louvers and fins, e.g., in the form including a frame forming a window, a plurality of tubular conduits within the window for carrying a coolant and fins between the conduits having louvers formed therein.

In certain implementations, the deactivation factor of the device is at least 0.50 at least 0.55 or at least 0.60 based on a radiator (e.g., an automobile radiator) with 16 mm depth and 63 cpsi. In other implementations, these parameters are obtained on a radiator is fitted with louvers and fins, e.g., in the form including a frame forming a window, a plurality of tubular conduits within the window for carrying a coolant and fins between the conduits having louvers formed therein.

The catalysis composition (e.g., ozone catalyst) of the present invention may be layered on from about 10% to about 100% of the substrate (e.g. radiator) surface or from about 60% to about 100% of the radiator surface.

The coating may be any suitable thickness, e.g., from about 1 to about 100 micrometers, from about 10 to about 50 micrometers or from about 15 to about 35 micrometers.

In certain aspects of the disclosure, the catalysis composition is the only material layered onto the substrate. In other implementations, the catalysis composition is the only catalysis material layered onto the substrate.

In certain aspects, there may be an overlayer on the catalyst coating or an underlayer between the substrate (e.g., radiator) and the catalyst coating. The underlayer or over layer may be a protective coat, an adhesion coat or an additional catalysis coat. The adhesion coat may be a latex material or an acrylic material. The protective coat may contain a protective substance which is stable at elevated temperatures (e.g., up to 120° C.) and may be resistant to chemicals, salts, dirt and other contaminants which may adversely affect the catalyst composition. The protective material may be, e.g., a plastic material such as polyethylene, polypropylene, polytetrafluoroethylene or a combination thereof.

When the catalysis composition is coated onto an automobile radiator, the device may have, e.g., less than about 6% impact on cooling efficiency as compared to an uncoated radiator, less than about 5% impact on cooling efficiency as compared to an uncoated radiator or less than about 3% impact on cooling efficiency as compared to an uncoated radiator.

In other implementations when the catalysis composition is coated onto an automobile radiator, the device may have, e.g., a washcoat weight loss of less than about 6%, or less than about 3% based on an ultrasonic adhesion test.

In further implementations when the catalysis composition is coated onto an automobile radiator, the device may have, e.g., less than about a 20% increase in pressure drop in a coated device as compared to a non-coated device, less than about a 15% increase in pressure drop in a coated device as compared to a non-coated device or less than about a 10% increase in pressure drop in a coated device as compared to a non-coated device.

The catalysis composition of the present invention may have a dispersion of catalyst, e.g., of from about 50% to about 95% or from about 60% to about 80% of manganese oxide crystallite domains measured less than 30 nanometers using the primary crystallite dimension of the domains within the high surface area support structure based on transmission electron microscopy.

In other implementations, the catalysis composition of the present invention may have a dispersion of catalyst, e.g., of from about 50% to about 95% or from about 60% to about 80% of manganese oxide crystallite domains measured less than 15 nanometers using the primary crystallite dimension of the domains within the high surface area support structure based on transmission electron microscopy.

In certain implementations, the disclosure is directed to a physical mixture of metal oxide catalysts particles and high surface area support particles such that separate domains of metal oxide and support can function independently as catalyst and aging protection respectively.

In other implementations, the disclosure is directed to an alloy of metal oxide catalysts and high surface area support such that the function of each material is inseparable from the other.

In other implementations, the disclosure is directed to a high surface area support particle which is in surface contact either within the pore structure and/or externally with small (<100 nm) domains of metal oxide catalysts such that separate domains of metal oxide can function independently as catalyst and are provided protection from aging mechanisms within the support material.

In other implementations, the disclosure is directed to a high surface area support particle which is externally coated with a porous shell structure of metal oxide catalyst material such that the metal oxide catalyst function is external to the support providing a high surface area interior to the composite particle.

In other implementations, the disclosure is directed to a high surface area support which is encompassing a metal oxide particle in a coating layer such that the metal oxide catalyst is entirely surrounded by a protective high surface area support material.

The present disclosure is also directed to methods of preparing a catalysis device including at least partially layering an ozone catalyst coating on an automobile radiator, wherein the catalyst coating including an ozone catalyst, a support material impregnated with the catalyst and the catalyst has a deactivation factor of at least 0.5.

In other implementations, the disclosure is directed to a method of preparing a catalysis device including at least partially layering an ozone catalyst coating on an automobile radiator, wherein the catalyst coating including an ozone catalyst, a support material impregnated with the catalyst, the catalyst has a deactivation factor of at least 0.5 is in amorphous form and the radiator does not include an additional catalyst layer or support layer.

The certain aspects, the coating step may include, e.g., spraying, powder coating, dip coating, electroplating, or electrostaticing a particulate support material in a solution of the catalyst onto the radiator. The solution may also include other agents such as a surfactant.

In a further implementation, the disclosure is directed to a method of preparing a catalyst composition including mixing particulate support material in a solution of a metal catalyst wherein the catalyst is impregnated in the support material in an amount of about 0.5 atoms to about 2.5 atoms per surface hydroxyl group of the support material.

In another implementation, the disclosure is directed to a method of preparing a catalysis device including at least partially layering a manganese acetate catalyst coating on an automobile radiator, wherein the catalyst coating including a metal catalyst and a support material impregnated with the catalyst and the catalyst has a deactivation factor of at least 0.5.

In another implementation, the disclosure is directed to a method of preparing a catalysis device including at least partially layering a manganese acetate catalyst coating on an automobile radiator, wherein the catalyst coating including a metal catalyst, a support material impregnated with the catalyst, the radiator does not include an additional catalyst layer or support layer and the catalyst has a deactivation factor of at least 0.5.

In another aspect, a catalysis composition includes a catalyst and a support material impregnated with the catalyst, such that the catalysis composition, when coated onto a substrate and contacted with an airstream having an initial ozone concentration, is adapted to convert ozone within the airstream such that a final ozone concentration of the airstream is reduced by greater than 30% of the initial ozone concentration after the catalysis composition is contacted with the airstream, and the catalysis composition has a deactivation factor of at least about 0.5.

In another aspect, a catalysis composition includes a catalyst and a support material impregnated with the catalyst, such that the catalysis composition, when coated onto a substrate and contacted with an airstream having an initial ozone concentration, is adapted to convert ozone within the airstream such that a final ozone concentration of the airstream is reduced by greater than 30% of the initial ozone concentration after the catalysis composition is contacted with the airstream. The initial ozone concentration ranges from about 0.1 ppm to about 1.2 ppm, a space velocity of the airstream ranges from about 200,000 hr$^{-1}$ to about 800,000 hr$^{-1}$, and a temperature of the airstream is maintained within a range of about 70° C. to about 80° C.

One aspect of the present disclosure is directed to a method of cleaning the atmosphere including contacting a composition or device as disclosed herein with an airstream including a pollutant and catalyzing the pollutant to a less toxic compound.

The device may be part of an automobile and the contacting with airstream is performed by operating the automobile.

The present disclosure is also directed to automobiles or automobile parts incorporating a composition or device as disclosed herein. The automobile part may be, e.g., selected from the group consisting of vehicle paint, wheel wells, bumpers, air conditioning components, grilles, fans, blades, shrouds, shutters, turbo intercoolers, gear box coolers, battery coolers, front end components, and a hood liner.

FIG. 1 illustrates a truck 100 schematically containing a variety of atmosphere contacting surfaces. The vehicle includes a grille 102, an air conditioner condenser 104, a radiator 106, and a radiator fan 108. These components are examples of automobile components that can be coated with the catalysis compositions disclosed herein. The air conditioning condenser 104 includes a front surface 104A and a side 105B surface, and the radiator 106 includes a front surface 106A and a side surface 106B. Each of these surfaces are located within a housing 110 of the truck. They are typically under the hood of the truck between the front 112 of the truck and an engine 114. The air conditioner condenser 104 and the radiator 106 can be directly or indirectly supported by the housing 110 or a frame (not shown) within the housing 110. One or more of these components may be coated with the catalysis compositions disclosed herein.

Figure 2:
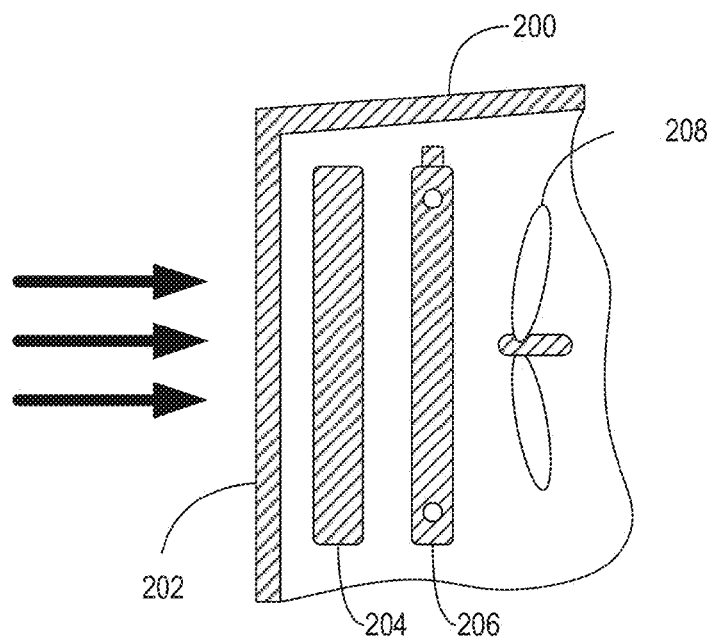
FIG. 2 depicts a side cross-sectional view of an automobile radiator-air conditioning condenser assembly in accordance with an implementation.

FIG. 2 depicts a side cross-sectional view of an automobile radiator-air conditioning condenser assembly in accordance with an implementation. The automobile includes a frame 200, which may be the same as the frame 110 described with respect to FIG. 1. A front end of the automobile includes a grille 202, which may be the same as the grille 102 described with respect to FIG. 1, and which is supported on the front of the frame 200. An air conditioner condenser 204, a radiator 206, and a radiator fan 208 may be located within the frame 200, and may be the same as their identically named counterparts of FIG. 1. One or more of these components may be coated with the base metal catalyst layers disclosed herein.

Figure 3:
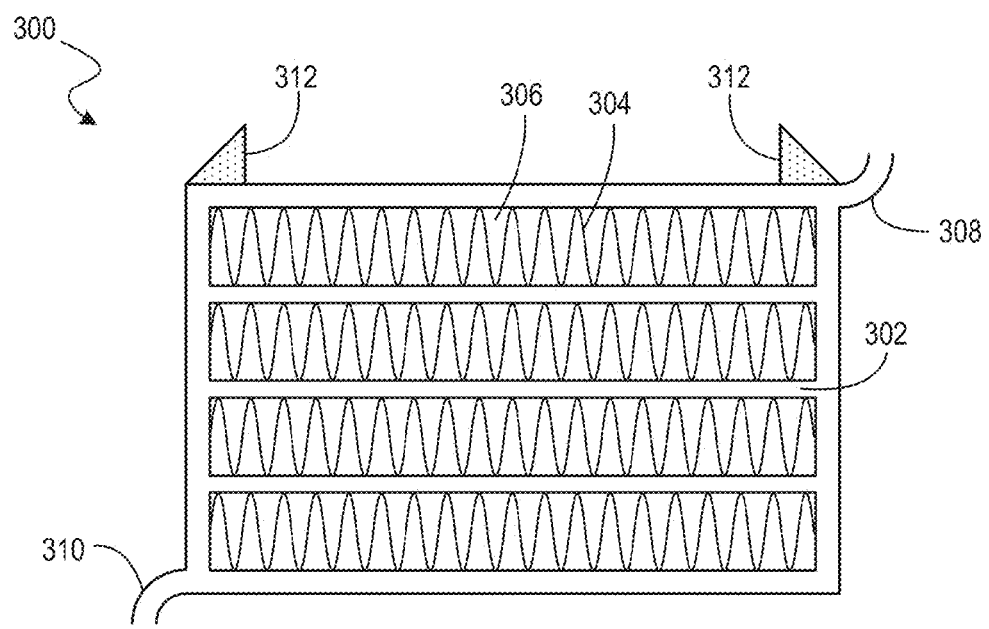
FIG. 3 depicts a partial perspective view of a radiator with fins coated with a catalyst layer in accordance with an implementation.

FIG. 3 depicts a partial perspective view of a radiator with fins coated with a catalyst layer in accordance with an implementation. A radiator 300 (which may be the same as radiator the 206 described with respect to FIG. 3B) may include spaced apart tubes 302 for the flow of a first fluid. The tubes are arranged horizontally through the radiator 300, and a series of corrugated plates 304 are inserted therebetween defining a pathway 306 for the flow of a second fluid transverse to the flow of the first fluid. The first fluid, such as antifreeze, is supplied from a source to the tubes 302 through an inlet 308. The antifreeze enters the radiator 300 at a relatively low temperature through the inlet 308, eventually leaves the radiator through an outlet 310, and may be recirculated. The second fluid may be ambient air that passes through the pathway 306 and exchanges heat with the first fluid passing through the tubes 302. The corrugated plates 304 may be coated with base metal catalyst layers (e.g., the catalyst layer 102 described with respect to FIG. 1) in order to convert or remove pollutants, such as ozone and volatile organic compounds, from the ambient air. In certain implementations, the radiator is provided with projections 312 (e.g., fins), which may be non-heat exchange surfaces directed along the air-flow path. In some implementations, one or more of the projections 312 are coated with a catalyst layer as disclosed herein (e.g. by spraying), such as a base metal catalyst. In certain implementations, the projections 312 are omitted.

Figure 4:
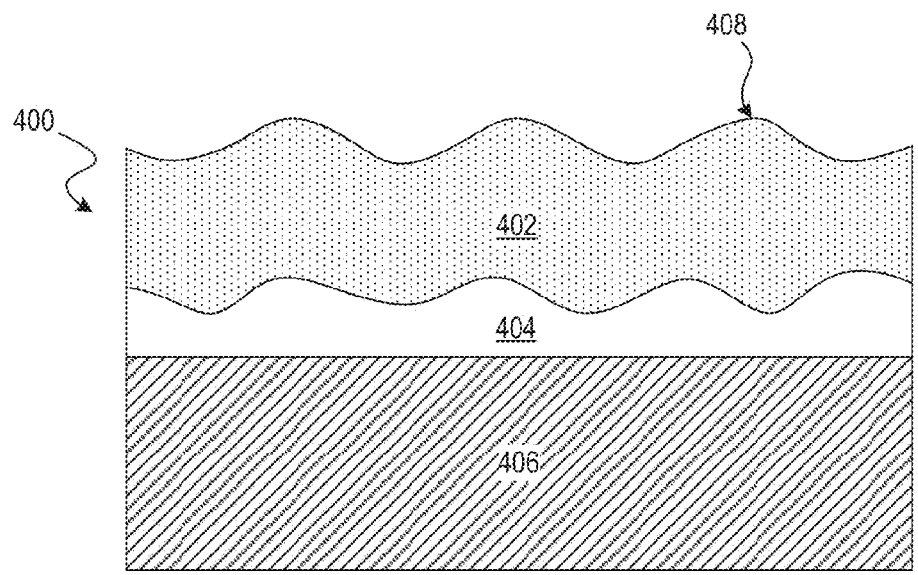
FIG. 4 depicts a cross sectional view of a catalyst layer deposited on a solid substrate in accordance with an implementation.
Figure 5:
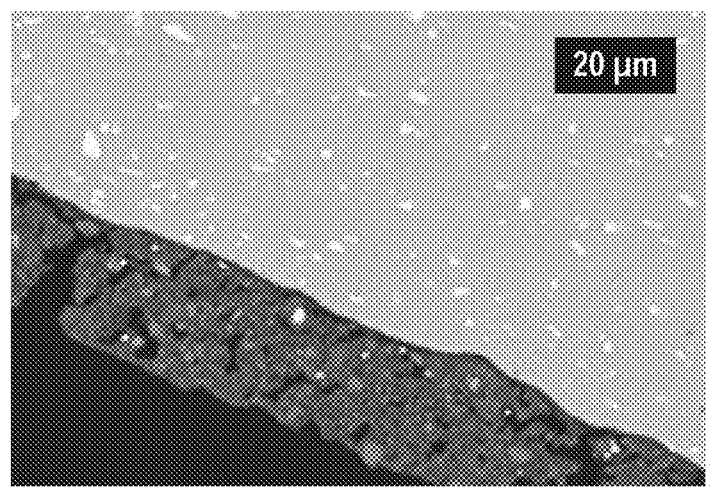
FIG. 5 is a micrograph of a catalyst layer coating on an aluminum radiator surface in accordance with an implementation.

FIG. 4 depicts a cross sectional view of a catalyst device 400 that includes a catalyst layer 402 deposited on a solid substrate 406 in accordance with an implementation. The catalyst device 400 is formed by coating a catalyst layer 402 onto the substrate 406, which may include an intervening adhesive layer 404 that adheres the catalyst layer 402 to the substrate 409. The catalyst layer 402 may be porous and may have a high surface area surface 408 that contacts an airstream. The high surface area surface 408 facilitates turbulent airstream in the vicinity of the catalyst layer 402 such to increase the amount of exposure of pollutants within the airstream to the catalyst layer 402. The catalyst layer 402 and the adhesive layer 404 are not shown to scale. A micrograph of a catalyst device formed in accordance with the implementations described herein is shown in FIG. 5.

In certain implementations, the catalyst layer 402 is a base metal catalyst. The base metal catalyst is prepared, for example, in the form of a slurry having target amounts of metal salts (e.g., acetate, nitrate, carbonate, sulfate based salts, or potassium permangante) mixed with a support material (e.g., ceria, lanthana, silica, alumina, or combinations thereof). After addition of one or more binders, the slurry may then be coated onto a substrate (e.g., the substrate 406) and calcined to produce the catalyst layer.

In some implementations, there may be an overlayer on the catalyst coating or an underlayer between the substrate and the catalyst layer 402. The underlayer or overlayer may be a protective coat, an adhesion layer (e.g., the adhesion layer 404), or an additional catalyst layer. The adhesion layer 404, for example, may be a latex material or an acrylic material. In certain implementations, the catalyst layer 402 is adhered directly to the substrate 406 without the use of the adhesion layer 404. The protective coat may contain a protective substance which is stable at elevated temperatures (e.g., up to 120° C.) and may be resistant to chemicals, salts, dirt and other contaminants that may adversely affect the catalyst composition. The protective material may include, for example, a plastic or polymeric material such as polyethylene, polypropylene, polytetrafluoroethylene, styrene acrylic, or a combination thereof.

In certain implementations, the catalyst layer 402 is a physical mixture of metal oxide catalysts particles and high surface area support particles such that separate domains of metal oxide and support can function independently as catalyst and aging protection, respectively.

In certain implementations, the catalyst layer 402 is an alloy of metal oxide catalysts and high surface area support such that the function of each material is inseparable from the other.

In certain implementations, the catalyst layer 402 is a high surface area support particle which is in surface contact either within the pore structure and/or externally with small (<100 nm) domains of metal oxide catalysts such that separate domains of metal oxide can function independently as catalyst and are provided protection from aging mechanisms within the support material.

In certain implementations, the catalyst layer 402 is a high surface area support particle which is externally coated with a porous shell structure of metal oxide catalyst material such that the metal oxide catalyst function is external to the support providing a high surface area interior to the composite particle.

In certain implementations, the catalyst layer 402 is a high surface area support which is encompassing a metal oxide particle in a coating layer such that the metal oxide catalyst is entirely surrounded by a protective high surface area support material.

In certain implementations, the catalyst layer 402 has a relatively high thermal conductivity while maintaining pollutant destruction efficiency. In certain implementations of the disclosure, high thermal conductivity materials (e.g., in the form of particles) may be blended into the coating to provide or enhance the thermal conductivity property of the coating without significantly impacting on diffusion through the coating. Non-limiting examples of such materials include metals such as aluminum, graphite, silicon carbide and sapphire. The material can be in the form of particles (e.g., flakes). The particle size may be any suitable size. In one implementation, the particles are on the order of the size of the catalyst and/or no more than the desired thickness of the coating. For example, the particles may have a mean size from about 1 micrometer to about 30 micrometers, or from about 1 micrometer to about 10 micrometers. The materials (e.g., particles) may be including in the coating in an amount of from about 1% to about 50% by mass of the total coating.

In some implementations, one or more binders may be added to a catalyst slurry to enhance washcoat adhesion. In some implementations, two different binders were added to the catalyst slurry, which yielded improved performance (in terms of weight loss) over the same quantity of the individual binders by themselves. An example catalysis composition included a first styrene acrylic binder ("Binder 1") and a second styrene acrylic binder ("Binder 2") mixed as shown in Table 1. Binder 1 was a styrene acrylic binder (Joncryl® 1530) having a glass transition temperature of 12° C. Binder 2 was a styrene acrylic binder (Joncryl® 1980) having a glass transition temperature of 78° C. Ultrasonic washcoat adhesion weight loss testing was performed in accordance with Example 15 discussed below. In some implementations, other types of binders may be used.

TABLE 1

Binder Ratios (mass %) and Associated Washcoat Adhesion Weight Loss After Coating

| Binder Composition | Average Loss, % |
|---|---|
| Binder 1 @ 12% | 2.50 |
| Binder 2 @ 12% | 1.70 |
| Binder 1 @ 6% + Binder 2 @ 6% | 1.10 |

In certain implementations of the present disclosure, a catalysis composition includes a metal catalyst and support material impregnated with the metal catalyst. The catalysis composition further includes a first binder and a second binder such that a washcoat weight loss of the catalysis composition after coating onto a substrate is less than about 1.6%. In some implementations, the washcoat weight loss of the catalysis composition after coating onto the substrate is less than about 1.3%. In some implementations, the washcoat weight loss of the catalysis composition after coating onto the substrate is less than about 1.15%. In one implementation, measuring the washcoat weight loss of the catalyst layer includes using an ultrasonic adhesion test.

In one implementation, a mass ratio of the first binder to the second binder ranges from about 0.75 to about 1.25. In one implementation, at least one of the first binder or second binder is a styrene acrylic binder.

In one implementation, the first binder has a first glass transition temperature ranging from about 5° C. to about 20° C., and the second binder has a second glass transition temperature that is greater than the first glass transition temperature. In one implementation, the first binder has a first glass transition temperature ranging from about 8° C. to about 15° C., and the second binder has a second glass transition temperature that is greater than the first glass transition temperature.

In one implementation, the first binder has a first glass transition temperature ranging from about 70° C. to about 90° C., and wherein the second binder has a second glass transition temperature that is less than the first glass transition temperature. In one implementation, the first binder has a first glass transition temperature ranging from about 75° C. to about 85° C., and wherein the second binder has a second glass transition temperature that is less than the first glass transition temperature.

In one implementation, the first binder has a first glass transition temperature ranging from about 5° C. to about 20° C., and the second binder has a second glass transition temperature ranging from about 70° C. to about 90° C. In one implementation, the first binder has a first glass transition temperature ranging from about 8° C. to about 15° C., and the second binder has a second glass transition temperature ranging from about 75° C. to about 85° C.

In one implementation, a first mass percent of the first binder within the catalysis composition is between about 4% and about 8%, and a second mass percent of the second binder within the catalysis composition is between about 4% and about 8%.

The following examples are set forth to assist in understanding the invention and should not, of course, be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

ILLUSTRATIVE EXAMPLES

Example 1

A manganese nitrate solution (50% w/w solution) was diluted to a volume matching the incipient wetness point of a high surface area gamma alumina support material (2.0 mL/g), referred to hereinafter as "Support(1)", and to a concentration matching the total desired manganese (Mn) content of the final solid (5.0 g of Mn). Support(1) is a gamma alumina and silica (19:1) support, and, as measured, has a BET surface area of 230 $m^2$/g, a pore volume of 1.2 mL/g, and average pore radius of 7.5 nanometers. The diluted Mn nitrate solution was slowly and completely added to the dry Support(1) solid (92.1 g) under mixing until reaching the incipient wetness point, forming Mn impregnated wet alumina. The Mn impregnated wet alumina was dried at 90° C. for 2 hours, and then calcined at 550° C. in a box furnace for one hour.

Example 2

A manganese nitrate solution (50% w/w solution) was diluted to a volume matching the incipient wetness point of Support(1) (2.0 mL/g), and to a concentration matching the total desired Mn content of the final solid (15.0 g of Mn). The diluted Mn nitrate solution was slowly and completely added to the dry Support(1) solid (76.3 g) under mixing until reaching the incipient wetness point, forming Mn impregnated wet alumina. The Mn impregnated wet alumina was then dried at 90° C. for 2 hours and then calcined at 550° C. in a box furnace for one hour.

Example 3

A manganese acetate solution (30% w/w solution) was prepared by dissolving $Mn(C_2H_3O_2)_2.4H_2O$ (60 g) in 100 mL of deionized water. The Mn acetate solution was diluted to a volume matching the incipient wetness point of Support (1) (2.0 mL/g), and to a concentration matching the total desired Mn content of the final solid (5.0 g of Mn). The diluted Mn acetate solution was slowly and completely added to dry Support(1) solid (92.1 g) under mixing until reaching the incipient wetness point, forming Mn impregnated wet alumina. The Mn impregnated wet alumina was then dried at 90° C. for 2 hours and then calcined at 550° C. in a box furnace for one hour.

Example 4

A manganese acetate solution (30% w/w solution) was prepared by dissolving $Mn(C_2H_3O_2)_2 \cdot 4H_2O$ (60 g) in 100 mL of deionized water. The Mn acetate solution was diluted to a volume matching the incipient wetness point of Support (1) (2.0 mL/g), and to a concentration matching the total desired Mn content of the final solid (15.0 g of Mn). The diluted Mn acetate solution was slowly and completely added to the dry Support(1) solid (76.3 g) under mixing until reaching the incipient wetness point, forming Mn impregnated wet alumina. The Mn impregnated wet alumina was then dried at 90° C. for 2 hours and then calcined at 550° C. in a box furnace for one hour.

Example 5

A manganese acetate solution (30% w/w solution) was prepared by dissolving $Mn(C_2H_3O_2)_2 \cdot 4H_2O$ (60 g) in 100 mL of deionized water. The manganese acetate solution was diluted into two separate solutions, each to volumes matching the incipient wetness point of a gamma alumina support material (1.1 mL/g), hereinafter referred to as "Support(2)", and to a concentration matching half the total desired Mn content of the final solid (14.0 g of Mn). Support(2) is a high surface area gamma alumina and silica (19:1) support with a measured BET surface area of 320 $m^2/g$ and a Barrett-Joyner-Halenda (BJH) pore volume of 0.8 mL/g. The diluted Mn acetate solution was slowly and completely added to the dry Support(2) solid (76.3 g) under mixing until reaching the incipient wetness point, forming Mn impregnated wet alumina. The Mn impregnated wet alumina was then dried at 90° C. for 2 hours, and then the impregnation procedure was repeated with the second Mn acetate solution in the same manner. The final wet alumina was then dried at 90° C. for 2 hours and then calcined at 550° C. in a box furnace for one hour.

Example 6

A solution containing manganese (30% w/w solution) and potassium (15% w/w solution) was prepared by dissolving $Mn(C_2H_3O_2)_2 \cdot 4H_2O$ (60 g) in 100 mL of deionized water and $K(C_2H_3O_2)$ (18 g) in 100 mL of deionized water. The manganese and potassium solution was diluted to a volume matching the incipient wetness point of Support(1) (2.0 mL/g) and to a concentration matching the total desired Mn content of the final solid (15.0 g of Mn). The diluted Mn and K acetate solution was slowly and completely added to the dry Support(1) solid (76.3 g) under mixing until reaching the incipient wetness point, forming Mn/K impregnated wet alumina. The Mn/K impregnated wet alumina was then dried at 90° C. for 2 hours and then calcined at 550° C. in a box furnace for one hour.

Example 7

A cobalt (Co) nitrate solution (20% w/w solution) was prepared by dissolving $Co(NO_3)_2 \cdot 6H_2O$ (60 g) in 100 mL of deionized water. The cobalt nitrate solution was diluted to a volume matching the incipient wetness point of Support(1) (2.0 mL/g) and to a concentration matching the total desired Co content of the final solid (5.0 g of Co). The diluted Co nitrate solution was slowly and completely added to the dry Support(1) solid (93.2 g) under mixing until reaching the incipient wetness point, forming Co impregnated wet alumina. The Co impregnated wet alumina was then dried at 90° C. for 2 hours and then calcined at 550° C. in a box furnace for one hour.

Example 8

A manganese acetate solution (30% w/w solution) was prepared by dissolving $Mn(C_2H_3O_2)_2 \cdot 4H_2O$ (60 g) in 100 mL of deionized water. The manganese acetate solution was diluted to volume matching the incipient wetness point of a gamma alumina support material (1.4 mL/g), hereinafter referred to as "Support(3)", and to concentration matching the total desired Mn content of the final solid (5.0 g of Mn). Support(3) is a high surface area gamma alumina and silica (19:1) support with measured BET surface area of 180 $m^2/g$ and a BJH pore volume of 0.85 mL/g. The diluted Mn acetate solution was slowly and completely added to the dry Support(3) solid (92.1 g) under mixing until reaching the incipient wetness point, forming Mn impregnated wet alumina. The Mn impregnated wet alumina was then dried at 90° C. for 2 hours and then calcined at 550° C. in a box furnace for one hour.

Example 9

A manganese acetate solution (30% w/w solution) was prepared by dissolving $Mn(C_2H_3O_2)_2 \cdot 4H_2O$ (60 g) in 100 mL of deionized water. The manganese acetate solution was diluted to a volume matching the incipient wetness point of a silica support material (2.76 mL/g), hereinafter referred to as "Support(4)", and to a concentration matching the total desired Mn content of the final solid (5.0 g of Mn). Support (4) is a high surface area silica support as measured has a BET surface area of 200 $m^2/g$. The diluted Mn acetate solution was slowly and completely added to the dry Support(4) solid (92.1 g) under mixing until reaching the incipient wetness point, forming Mn impregnated wet silica. The Mn impregnated wet silica was then dried at 90° C. for 2 hours and then calcined at 550° C. in a box furnace for one hour.

Example 10

A manganese acetate solution (30% w/w solution) was prepared by dissolving $Mn(C_2H_3O_2)_2 \cdot 4H_2O$ (60 g) in 100 mL of deionized water. The manganese acetate solution was diluted to a volume matching the incipient wetness point of Support(1) (2.0 mL/g) and to a concentration matching the total desired Mn content of the final solid (15.0 g of Mn). The diluted Mn acetate solution was slowly and completely added to the dry Support(1) solid (76.3 g) under mixing until reaching the incipient wetness point, forming Mn impregnated wet alumina. The Mn impregnated wet alumina was then fed directly into a flash calcination reaching 550° C. in under 1 minute.

Example 11

A manganese nitrate solution (50% w/w solution) was diluted to a volume matching the incipient wetness point of Support(1) (2.0 mL/g) and to a concentration matching the total desired Mn content of the final solid (15.0 g of Mn). The diluted Mn nitrate solution was slowly and completely added to the dry Support(1) solid (76.3 g) under mixing until reaching the incipient wetness point, forming Mn impregnated wet alumina. The Mn impregnated wet alumina was then fed directly into a flash calcination reaching 550° C. in under 1 minute.

Example 12

A manganese acetate solution (15% w/w solution) was prepared by dissolving $Mn(C_2H_3O_2)_2.4H_2O$ (67 g) in 225 mL of deionized water. The Mn acetate solution was mixed with Support(1) (76.3 g) to form a slurry with a concentration of Mn matching the total desired Mn content of the final solid (15.0 g of Mn). The diluted Mn acetate and Support(1) slurry was dried at 90° C. and then calcined at 550° C. in a box furnace for one hour.

Example 13

A catalyst was prepared using bulk manganese oxide powder with high surface area with a BET surface area of 240 $m^2/g$ and a BJH pore volume of 0.39 mL/g. This Mn oxide catalyst is of a cryptomelane type structure as described in U.S. Pat. No. 6,517,899.

Example 14: Catalyst Slurry Composition

Catalysts prepared according to Examples 3, 4, and 10-13 were used to prepare water based slurries for coating of substrates. Dry catalyst solids were mixed with polyacid dispersant (Rhodoline® 226/35 at 5% dry solids based on catalyst) and water (total solids about 30%) in a ball mill apparatus. The slurry was ball milled to a particle size of 50%<5 micrometers. The ball milled material was then blended with a styrene acrylic binder in a water based slurry (at 10% dry solids based on catalyst) to form a slurry with minimal adhesion properties for coating of substrates. Additional slurry components (such as xanthum gum and other surfactants) at levels <1% dry solids including binders, dispersants, and suspension aids were selected from those included in U.S. Pat. No. 6,517,899, which is hereby incorporated by reference herein in its entirety. The compositions were coated onto radiator segments of an aluminum Mitsubishi Radiator (Denso Part # AA422133-0501) using a hand dip procedure. Radiator segments (about 0.5 $in^2$ frontal surface area) were dipped in catalyst slurries, and the excess was blown out with an air gun and dried at 90° C. with target dry gain loadings of 0.40 $g/in^3$.

Example 15: Ultrasonic Adhesion Testing Method

Catalyst compositions prepared according to example 14 were tested for adhesion according to an ultrasonic procedure method. Coated radiator segments were immersed in deionized water and exposed to ultrasonic waves at 25 kHz and 500 Watts for 5 minutes. The segments were then dried at 90° C., and the weight difference before and after ultrasonic treatment was measured determining the total loss of coated material relative to the initial weight of the coated segment using a triplicate sample set.

Example 16: Catalyst Powder Ozone Conversion Testing Method

A powder testing method in which the catalyst materials prepared according to examples 1-13 were exposed to an airstream containing a given concentration of ozone (about 0.6 ppm to about 0.9 ppm). A sample of 20 mg of catalyst material was pelletized and sieved between 250 micrometer and 425 micrometer particles, and then mixed with an inert material to a volume of about 0.33 mL. Ozone concentration levels in the airstream, flowed at a space velocity of about 1,500,000 $hr^{-1}$ and a temperature of 35° C., were measured before and after the exposure to the catalyst powder. As used herein, "space velocity" refers to a volumetric ratio of an airstream flow to volume of a catalyst-coated substrate.

Example 17: Catalyst Powder Ozone Conversion Testing Results

Results shown in Table 2 below indicate that Example 4 has the highest activity according to the powder testing method of Example 16. In comparing Examples 2 and 4, as well as Examples 1 and 3, results indicate the Mn acetate solution used for Mn impregnation produces catalysts more active for ozone conversion than those prepared using Mn nitrate solutions. In addition, it was demonstrated that higher levels of Mn on the catalyst support produce catalysts that are more active for ozone conversion.

TABLE 2

| Sample | Ozone Conversion |
| --- | --- |
| | Ozone Conversion, % |
| Example 1 | 19.1 |
| Example 2 | 28.8 |
| Example 3 | 30.9 |
| Example 4 | 35.9 |

Example 18: Radiator Ozone Conversion Testing Method

Catalyst slurry compositions were prepared according to example 14 for catalysts 3, 4, and 10-13 and tested with an airstream containing a given concentration of ozone (about 0.1 ppm to about 1.2 ppm) passed through the coated radiator segments at face velocities typical of driving speeds (ranging from about 15 mph to about 30 mph). Ozone concentration levels in the airstream were measured before and after the coated radiator segment. The air temperature was maintained at about 75° C. with humidity dewpoint levels at both −15° C. and +15° C.

Example 19: Accelerated Aging (150 k) Method

Figure 6B:
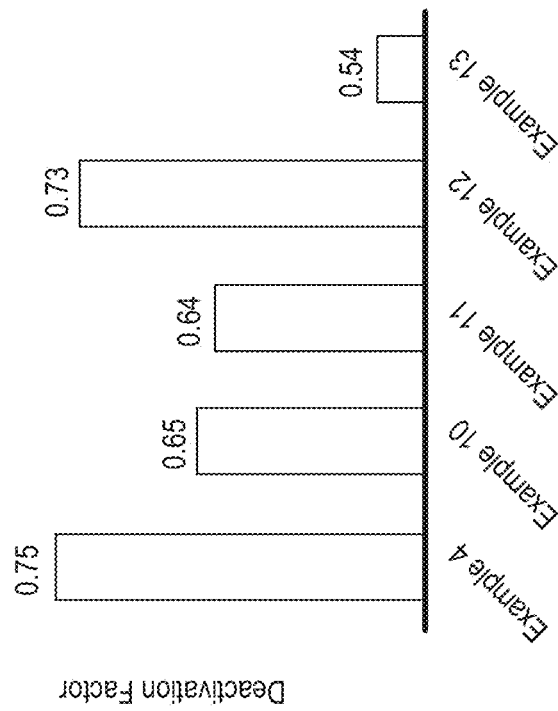
FIG. 6B is another plot showing deactivation factors for catalysts prepared in accordance various example implementations.
Figure 6A:
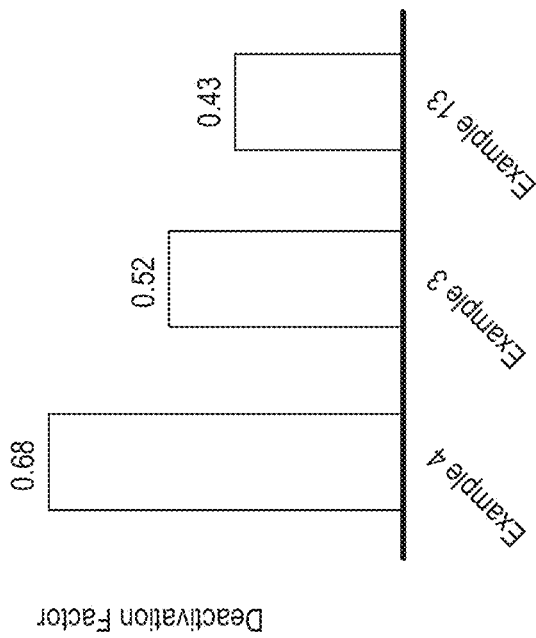
FIG. 6A is a plot showing deactivation factors for catalysts prepared in accordance various example implementations.

In referring to the term "deactivation factor, as it applies to automobile radiator coatings, the "aged % conversion" is defined (in certain implementations) as the percent conversion after the exposure to the equivalent of 150,000 miles of driving time. In order to rapidly simulate the effects of 150,000 miles of driving exposure, an accelerated aging test for catalyst coatings is employed. The coated radiator segment is inserted into an enclosed system with a controlled airstream that contains a high concentration of aerosol particles that is flowed over the radiator over a shortened period of time. Initially, of two radiators coated using identical methods, such as modified procedures as described in U.S. Pat. No. 6,517,899 and U.S. Pat. No. 6,555,079 (both of which hereby incorporated by reference herein in their entireties), one coated radiator was exposed to 150,000 miles of on road aging and the other exposed to the accelerated aging test. As an example, a Ford *Taurus* radiator with a 1" depth and 49 cells per square inch (cpsi) was exposed to the accelerated aging test and exhibited a deactivation factor 0.49. This accelerated aging test provides the aged % conversion value necessary for calculating the deactivation factors illustrated in FIGS. 6A and 6B. FIG. 6A corresponds to aging test results for a 16 mm depth radiator with 63 cpsi. FIG. 6B corresponds to aging test results for a 26 mm depth radiator with 49 cpsi. In both tests, Example 4 had the best performance after aging.

Example 20: Morphological Analysis

Various physical properties of manganese-based catalysis compositions were measured, including manganese content, surface area, pore volume, average pore radius, manganese structure, and manganese dispersion. Some of these properties are summarized for various example compositions in Table 3 below. Overall manganese content was determined by measuring x-ray fluorescence (XRF). In some implementations, a catalysis composition included a manganese content (mass %) ranging from about 14% to about 16%. In some implementations, the manganese content ranges from about 12% to about 18%. In some implementations, the manganese content ranges from about 5% to about 30%. In some implementations, the manganese content ranges from about 10% to about 25%.

TABLE 3

Catalyst Morphological Properties

| Sample | Mn Precursor | Mn Content (XRF), % | Surface Area (BET), m²/g | Pore volume (BJH), mL/g | Avg. Pore Radius (BJH), nm |
|---|---|---|---|---|---|
| Example 4 | Acetate | 14.78 | 193.8 | 0.90 | 7.65 |
| Example 10 | Nitrate | 14.26 | 222.7 | 0.73 | 5.26 |
| Example 11 | Acetate | 12.82 | 219.4 | 0.77 | 5.59 |
| Example 12 | Acetate | 14.68 | 188.1 | 0.86 | 6.98 |

X-ray photoelectron spectroscopy (XPS) was used to measure the surface Mn content of various catalysis compositions. XPS provides a measure of the Mn dispersion by comparing a mass of Mn detectable near the surface of the catalysis composition (e.g., within about 10 nanometers of the surface) versus the overall mass of Mn contained in the bulk (referred to herein as a "dispersion ratio"). Catalysis compositions, as prepared in accordance with the implementations described herein, may have dispersion ratios of at least about 13%. In some implementations, the dispersion ratio is at least about 15%. In some implementations, the dispersion ratio is at least about 30%. In some implementations, the dispersion ratio is at least about 50%.

XPS measurements were conducted using a K-Alpha™+ x-ray photoelectron spectrometer system (Thermo Scientific) with an aluminium K-α X-ray source. Powder samples were loaded onto carbon tape and outgassed for 2 hours prior to analysis. After an initial survey scan of the sample surface from 0-1350 eV, targeted high resolution scans of identified elements were conducted using a constant pass energy of 40.0 eV. The binding energies were referenced to the adventitious C1s peak, 284.8 eV. Shirley background and mixed Gaussian-Lorentzian line shapes were used to fit the resulting XPS spectra. Relative atomic percentages were then determined using the fitted peak data and sensitivity factors of each element (provided by Avantage software).

The pore structure of the supported catalyst, including both the pore volume and pore width, as well as surface area of the catalysis compositions were measured using a Micrometrics® TriStar 3000 Series instrument. Samples were prepared using an initial degassing cycle under $N_2$ with a 2 hour ramp rate up to 300° C. and a 4 hour soak time at 300° C. For surface area values, a 5 point BET measurement was used with partial pressures of 0.08, 0.11, 0.14, 0.17, and 0.20. Cumulative pore volume and average pore radius measurements were obtained from a BJH multipoint $N_2$ desorption/adsorption isotherm analysis using only pores with radii between 1.0 and 30.0 nm.

Figure 7A:
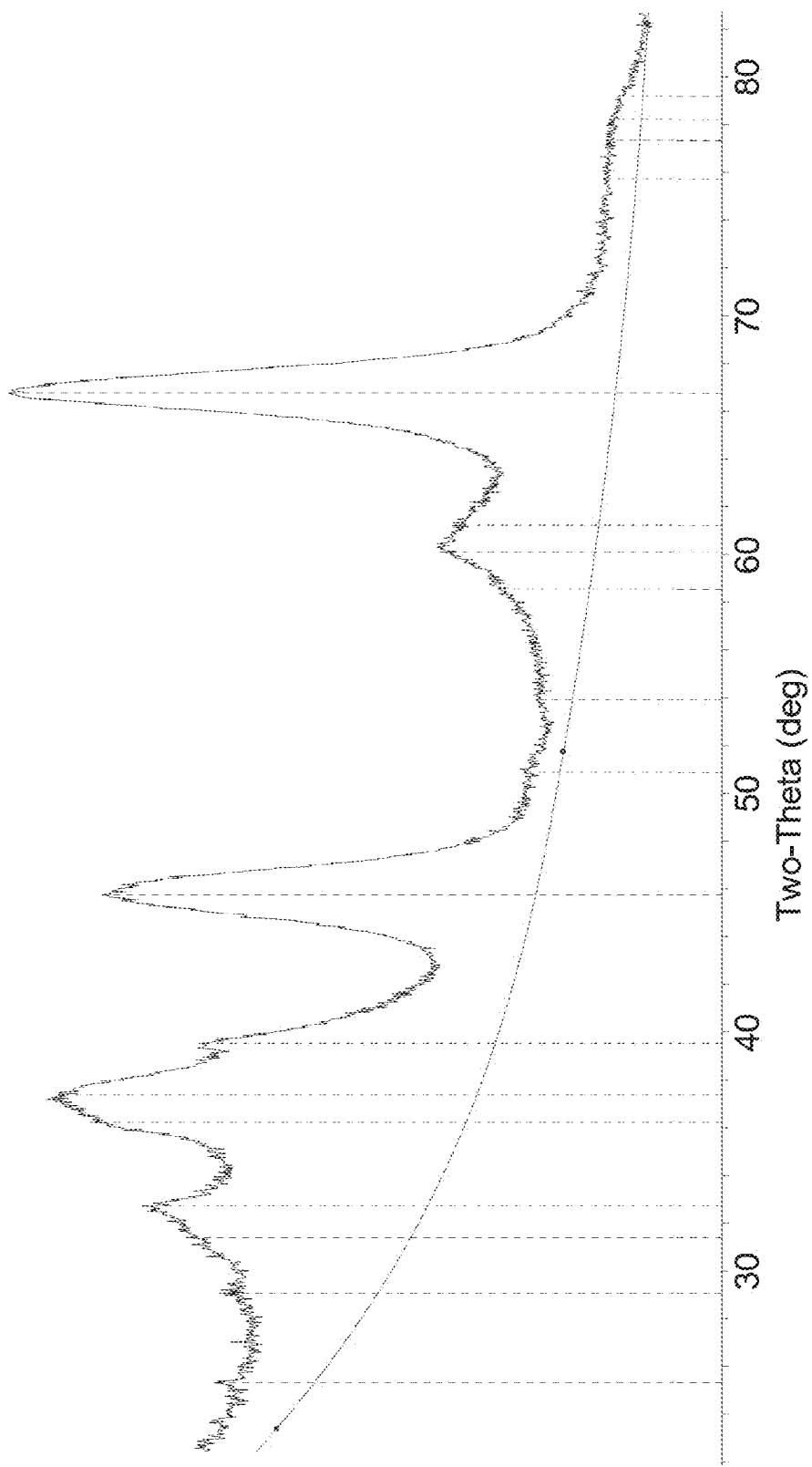
FIG. 7A is an x-ray diffraction spectrum of an alumina support.
Figure 7B:
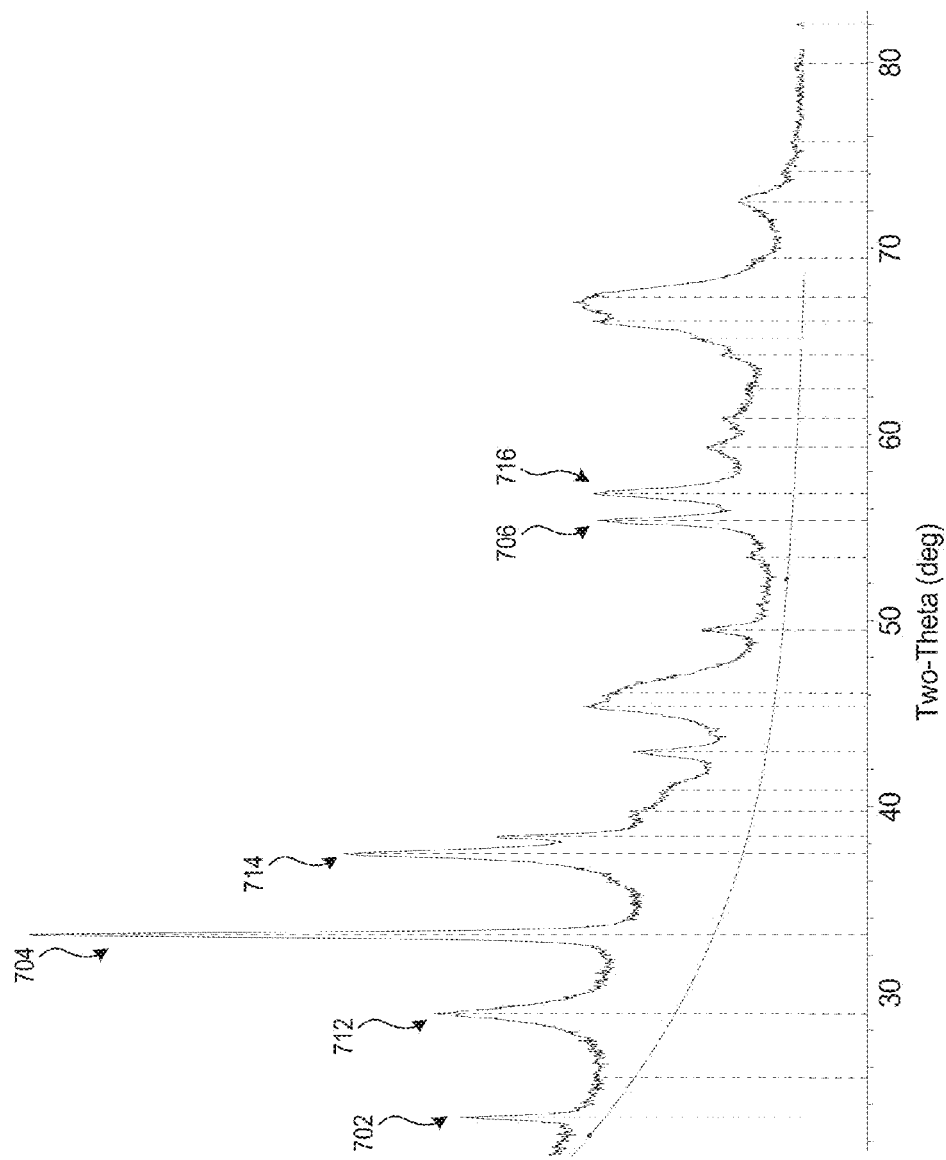
FIG. 7B is an x-ray diffraction spectrum of a catalyst prepared according to an implementation.
Figure 7C:
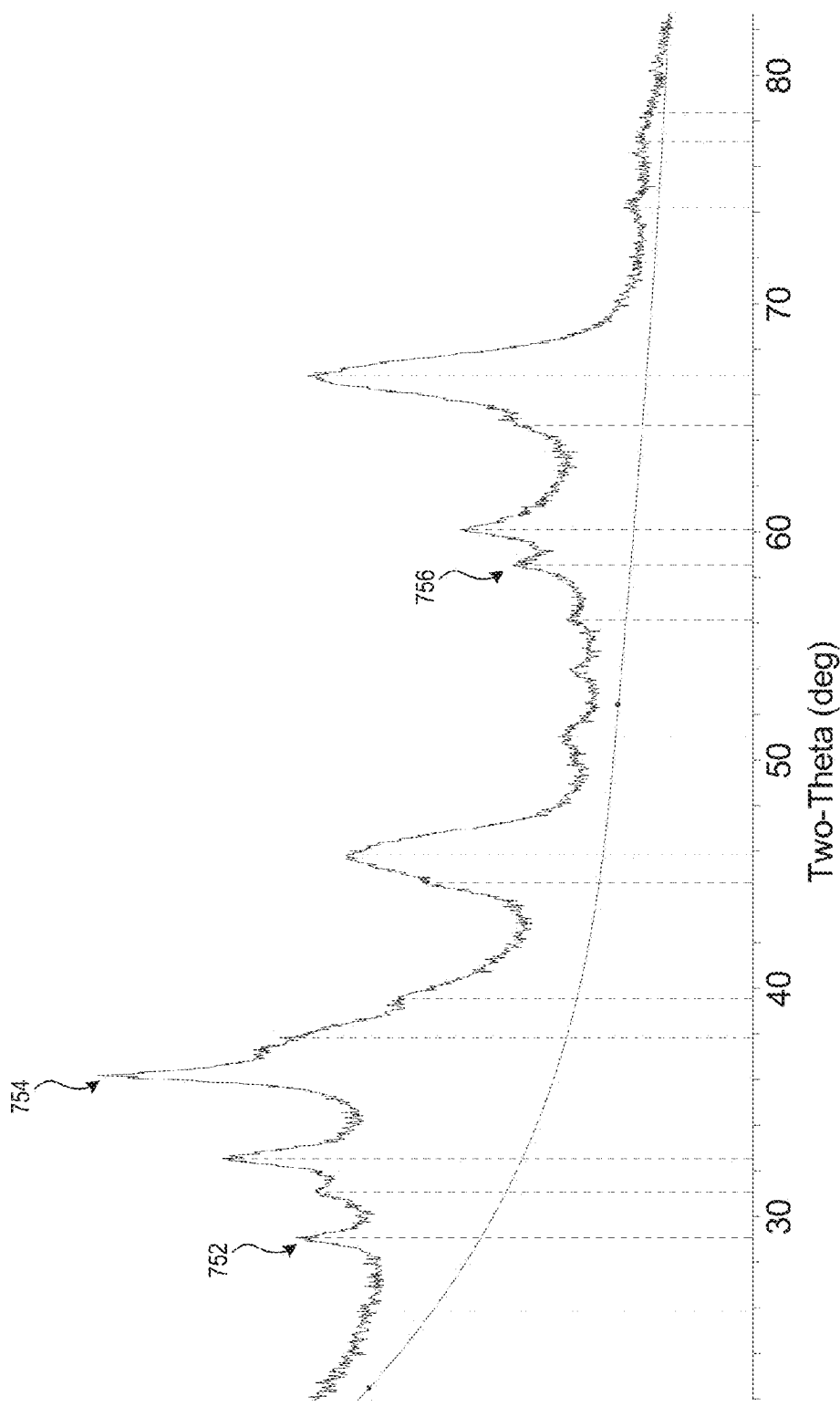
FIG. 7C is an x-ray diffraction spectrum of a catalyst prepared according to another implementation.

Using x-ray diffraction (XRD), the resulting spectra showed characteristic peaks of small manganese oxide crystallites. FIG. 7A shows a control spectrum corresponding to Support(1). FIGS. 7B and 7C are spectra corresponding to Examples 3 and 4, respectively, with peaks representative of Support(1) being present in each. As shown in FIG. 7B, peaks 702, 704, 706 are representative of pyrolusite ($MnO_2$) crystallites, while peaks 712, 714, 716 are representative of bixbyite ($Mn_2O_3$) crystallites. As shown in FIG. 7C, peaks 752, 754, 756 are representative of hausmannite ($Mn_3O_4$) crystallites. XRD measurements were obtained from powder samples using a PANalytical X'Pert Pro MPD diffraction system collecting data in Bragg-Brentano geometry, using $Cu_{K\alpha}$ radiation in the analysis with generator settings of 45 kV and 40 mA. Data was collected from 10° to 90° 2θ using a step size of 0.026° 2θ and a count time of 600 s per step. Jade Plus 9 analytical XRD software was used for phase identification.

The manganese oxide structure of certain catalysis compositions was measured by XRD. Some catalysis compositions had crystallites that were nearly undetectable by XRD. In some implementations, the catalysis composition performance (e.g., in terms of ozone conversion) appeared to be greater for catalysis compositions with smaller crystallite sizes (e.g., less than 10 nm). Without being bound by theory, it is believed that larger crystallite domains correspond to poorly dispersed magnesium oxide. In some implementations, manganese oxide crystallites included one or more of hausmannite ($Mn_3O_4$), manganosite (MnO), bixbyite ($Mn_2O_3$), or pyrolusite ($MnO_2$).

An estimate of crystallite size can be computed based on the Scherrer equation:

$$\tau = \frac{K\lambda}{\beta \cos\theta},$$

where:

$\tau$ is the average size of the crystalline domains;

K is a dimensionless shape factor, with a value close to unity (typically assumed to be 0.9);

$\lambda$ is the x-ray wavelength;

$\beta$ is the line broadening at half the maximum intensity (FWHM), after subtracting the instrumental line broadening, in radians; and $\theta$ is the Bragg angle.

The FWHM of the characteristic peaks in the 2θ range of 30° to 50° was used in the Scherrer equation to estimate crystallite size, as shown in Table 4. In some implementations, the average crystallite size was less than 30 nm, less than 20 nm, or less than 10 nm.

TABLE 4

Crystallite Sizes as Measured by XRD

| Sample | Mn$_2$O$_3$ Crystallite Size (nm) | MnO$_2$ Crystallite Size (nm) | Mn$_3$O$_4$ Crystallite Size (nm) |
|---|---|---|---|
| Example 3 | 26.4 | 8.6 | — |
| Example 4 | — | — | 9.4 |

Additional Implementations

Figure 8:
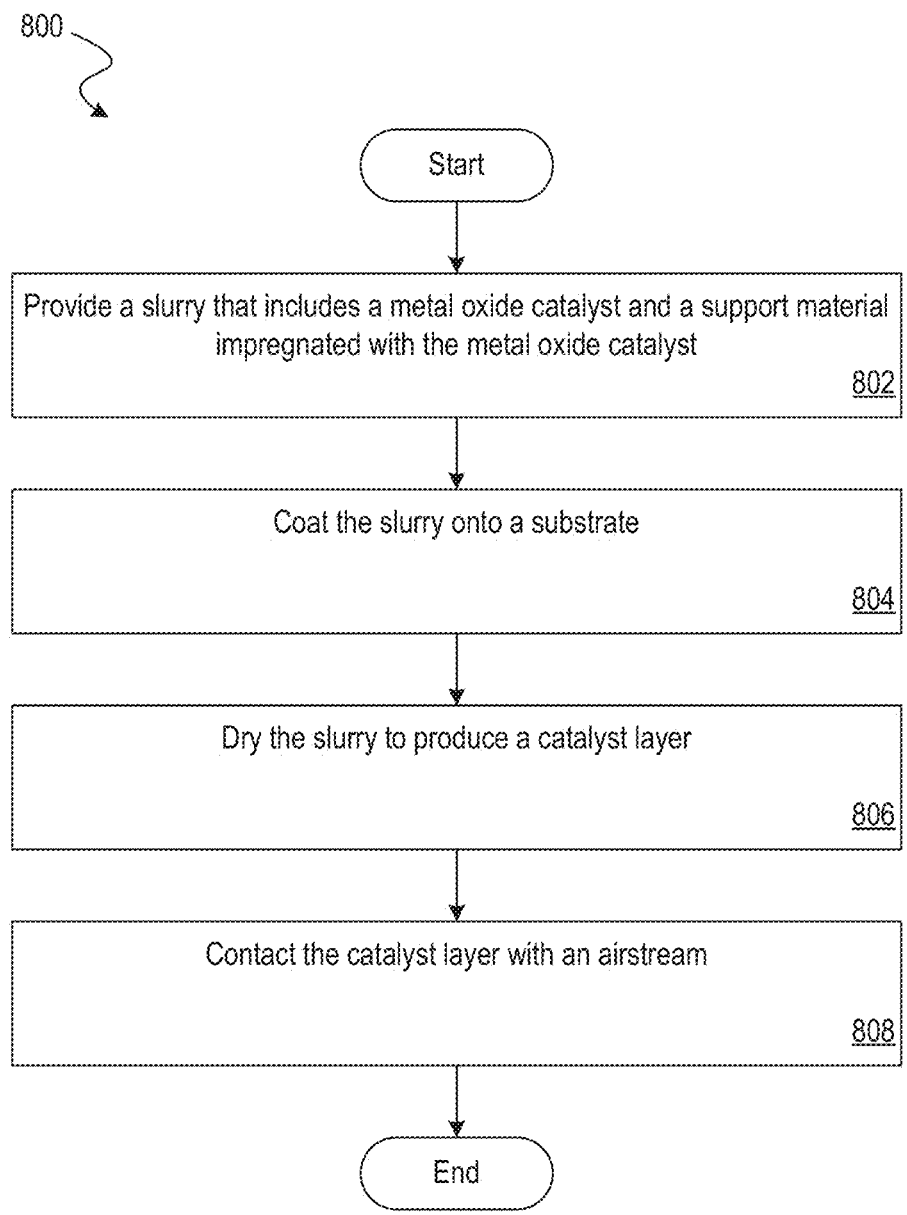
FIG. 8 is a flow diagram illustrating a method for producing a catalyst device in accordance with an implementation.

FIG. 8 is a flow diagram illustrating a method 800 for producing a catalyst device in accordance with an implementation. At block 802, a slurry is provided. The slurry includes a metal catalyst and a support material impregnated with the metal catalyst. In one implementation, the slurry contains additional metal oxide catalysts, or one or more metal-based catalysts in lieu of a metal oxide catalyst. The slurry may be prepared in accordance with any of the implementations described herein. In one implementation, the metal oxide catalyst is at least partially derived from a manganese acetate precursor.

In one implementation, the metal oxide catalyst is impregnated in the support material in an amount of about 1 atom to about 1.5 atoms per surface hydroxyl group of the support material. In one implementation, the metal oxide catalyst includes a base metal oxide selected from a group consisting of iron, copper, chromium, zinc, manganese, cobalt, nickel, compounds containing the same, and combinations thereof. In one implementation, the support material is selected from a group consisting of ceria, lanthana, alumina, titania, silica, zirconia, carbons, metal organic framework, clay, zeolites, and combinations thereof.

In one implementation, the metal oxide catalyst is impregnated in the support material such that at least about 15% of a total number of atoms in the metal oxide catalyst are detectable by surface XPS. In one implementation, the catalyst is impregnated in the support material such that at least about 30% of the total number of atoms in the metal oxide catalyst are detectable by surface XPS. In one implementation, the metal oxide catalyst is impregnated in the support material such that at least about 50% of the total number of atoms in the metal oxide catalyst are detectable by surface XPS. In one implementation, all atoms detectable by surface XPS are within about 10 nanometers from a surface of the catalysis composition at which the surface XPS is performed.

In one implementation, a cumulative pore volume of the catalysis composition is at least about 0.60 mL/g. In one implementation, the cumulative pore volume of the catalysis composition is at least about 0.70 mL/g. In one implementation, the cumulative pore volume of the catalysis composition is at least about 0.80 mL/g. In one implementation, the cumulative pore volume of the catalysis composition is at least about 0.85 mL/g. In one implementation, an average pore radius of the catalysis composition ranges from about 6 nanometers to about 15 nanometers. In one implementation, the average pore radius of the catalysis composition ranges from about 6 nanometers to about 10 nanometers. In one implementation, the average pore radius of the catalysis composition ranges from about 6 nanometers to about 8 nanometers. In one implementation, an average pore volume of the metal catalyst is greater than 0.70 mL/g.

In one implementation, the metal oxide catalyst includes manganese oxide crystallites. In one implementation, the metal oxide catalyst includes at least one of Mn$_3$O$_4$ crystallites or MnO crystallites. In one implementation, an x-ray diffraction spectrum of the catalysis composition includes at least one characteristic peak including at least one of a manganosite peak, pyrolusite peak, a bixbyite peak, or a hausmannite peak. In one implementation, the at least one characteristic peak includes a pyrolusite peak and a bixbyite peak. In one implementation, the at least one characteristic peak includes a pyrolusite peak and a hausmannite peak. In one implementation, the at least one characteristic peak includes a bixbyite peak and a hausmannite peak. In one implementation, the at least one characteristic peak includes a bixbyite peak, a pyrolusite peak, and a hausmannite peak. In one implementation, the characteristic peaks correspond to crystallite domains having average diameters of less than about 20 nanometers (e.g., as determined using the Scherrer equation).

In one implementation, the catalysis composition, when coated onto a substrate and contacted with an airstream having an initial ozone concentration, is adapted to convert ozone within the airstream such that a final ozone concentration of the airstream is reduced by greater than 30% of the initial ozone concentration after the catalysis composition is contacted with the airstream. In some implementations, the final ozone concentration of the airstream is reduced by greater than 40% of the initial ozone concentration. In some implementations, the final ozone concentration of the airstream is reduced by greater than 50% of the initial ozone concentration. In some implementations, the final ozone concentration of the airstream is reduced by greater than 60% of the initial ozone concentration. In some implementations, the final ozone concentration of the airstream is reduced by greater than 70% of the initial ozone concentration. In some implementations, final ozone concentration of the airstream is reduced by greater than 80% of the initial ozone concentration. In some implementations, the final ozone concentration of the airstream is reduced by greater than 90% of the initial ozone concentration. In one implementation, the initial ozone concentration ranges from about 0.1 ppm to about 1.2 ppm. In one implementation, the initial ozone concentration ranges from about 0.1 ppm to about 0.9 ppm. In one implementation, the initial ozone concentration ranges from about 0.6 ppm to about 0.9 ppm. In one implementation, a space velocity of the airstream ranges from about 200,000 hr$^{-1}$ to about 800,000 hr$^{-1}$. In one implementation, a temperature of the airstream is maintained within a range of about 70° C. to about 80° C.

In one implementation, a surface area of the catalysis composition is at least about 50 m$^2$/g. In one implementation, the surface area is at least about 100 m$^2$/g. In one implementation, the surface area is at least about 160 m$^2$/g. In one implementation, the surface area ranges from about 50 m$^2$/g to about 5000 m$^2$/g. In one implementation, the surface area ranges from about 100 m$^2$/g to about 300 m$^2$/g. In one implementation, the surface area ranges from about 100 m$^2$/g to about 200 m$^2$/g.

At block 804, the slurry is coated onto a substrate. In one implementation, the substrate is an automobile component selected from a group consisting of vehicle paint, a wheel well, a bumper, an air conditioning component, a grille, a fan, a fan blade, a shroud, a shutter, a turbo intercooler, a gear box cooler, a front end component, a radiator, and a hood liner. In one implementation, the catalysis composition, when coated onto the substrate, has a deactivation factor of at least 0.5. In one implementation, coating the slurry onto the substrate includes dipping the substrate into the slurry.

At block 806, the slurry is dried to produce a catalyst layer. In one implementation, coating the slurry onto the substrate includes drying the slurry at a temperature ranging from about 80° C. to about 120° C. to produce the catalyst layer. In one implementation, a washcoat adhesion weight loss of the substrate is measured using an ultrasonic adhesion test.

At block 808, the catalyst layer is contacted with an airstream. In one implementation, the contacting of the catalyst layer with the airstream is performed by operating the automobile. In one implementation, the contacting of the catalyst layer with the airstream is performed using a testing apparatus.

For simplicity of explanation, the embodiments of the methods of this disclosure are depicted and described as a series of acts. However, acts in accordance with this disclosure can occur in various orders and/or concurrently, and with other acts not presented and described herein. Furthermore, not all illustrated acts may be required to implement the methods in accordance with the disclosed subject matter. In addition, those skilled in the art will understand and appreciate that the methods could alternatively be represented as a series of interrelated states via a state diagram or events.

In the foregoing description, numerous specific details are set forth, such as specific materials, dimensions, processes parameters, etc., to provide a thorough understanding of the present invention. The particular features, structures, materials, or characteristics may be combined in any suitable manner in one or more embodiments. The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Reference throughout this specification to "an implementation", "certain implementations", or "one implementation" means that a particular feature, structure, or characteristic described in connection with the implementation is included in at least one implementation. Thus, the appearances of the phrase "an implementation", "certain implementations", or "one implementation" in various places throughout this specification are not necessarily all referring to the same implementation.

The term "about", when referring to a physical quantity, is to be understood to include measurement errors within, and inclusive of 2%. For example, "about 100° C." should be understood to mean "100±1° C."

The present invention has been described with reference to specific exemplary embodiments thereof. The specification and drawings are, accordingly, to be regarded in an illustrative rather than a restrictive sense. Various modifications of the invention in addition to those shown and described herein will become apparent to those skilled in the art and are intended to fall within the scope of the appended claims.

What is claimed is:

1. A catalysis composition comprising:
   a manganese oxide catalyst, wherein at least 50% of the manganese oxide catalyst is in amorphous form;
   a support material impregnated with the manganese oxide catalyst;
   a first binder; and
   a second binder, wherein,
   a coating of the catalysis composition on a substrate exhibits an ultrasonic washcoat adhesion weight loss of less than 1.60%, wherein
   the support material is selected from a group consisting of ceria, lanthana, alumina, titania, silica, zirconia, carbons, metal organic framework, clay, zeolites, and combinations thereof;
   wherein a cumulative pore volume of the catalysis composition is from about 0.80 mL/g to about 2.0 mL/g, an average pore radius of the catalysis composition is from about 6 nanometers to about 15 nanometers and a surface area of the catalysis composition is from about 100 m$^2$/g to about 200 m$^2$/g;
   wherein the manganese oxide catalyst is impregnated in the support material in an amount ranging from about 10% to about 25% metal atoms by mass, based on the total composition;
   the weight loss is weight difference of the coated substrate after being immersed in deionized water and exposed to ultrasonic waves at 25 kHz and 500 Watts for 5 minutes and dried at 90° C., and
   wherein the first binder has a first glass transition temperature ranging from about 5° C. to about 20° C., and wherein the second binder has a second glass transition temperature that is greater than the first glass transition temperature; or
   wherein the first binder has a first glass transition temperature ranging from about 70° C. to about 90° C., and wherein the second binder has a second glass transition temperature that is less than the first glass transition temperature.

2. The catalysis composition of claim 1, wherein the ultrasonic washcoat adhesion weight loss of the substrate is less than about 1.30%.

3. The catalysis composition of claim 1, wherein the ultrasonic washcoat adhesion weight loss of the substrate is less than about 1.15%.

4. The catalysis composition of claim 1, wherein a mass ratio of the first binder to the second binder ranges from about 0.75 to about 1.25.

5. The catalysis composition of claim 1, wherein at least one of the first binder or second binder is a styrene acrylic binder.

6. The catalysis composition of claim 1, wherein the first binder has a first glass transition temperature ranging from about 5° C. to about 20° C., and wherein the second binder has a second glass transition temperature that is greater than the first glass transition temperature.

7. The catalysis composition of claim 1, wherein the first binder has a first glass transition temperature ranging from about 8° C. to about 15° C., and wherein the second binder has a second glass transition temperature that is greater than the first glass transition temperature.

8. The catalysis composition of claim 1, wherein the first binder has a first glass transition temperature ranging from about 70° C. to about 90° C., and wherein the second binder has a second glass transition temperature that is less than the first glass transition temperature.

9. The catalysis composition of claim 1, wherein the first binder has a first glass transition temperature ranging from about 75° C. to about 85° C., and wherein the second binder has a second glass transition temperature that is less than the first glass transition temperature.

10. The catalysis composition of claim 1, wherein the first binder has a first glass transition temperature ranging from about 5° C. to about 20° C., and wherein the second binder has a second glass transition temperature ranging from about 70° C. to about 90° C.

11. The catalysis composition of claim 1, wherein the first binder has a first glass transition temperature ranging from about 8° C. to about 15° C., and wherein the second binder has a second glass transition temperature ranging from about 75° C. to about 85° C.

12. The catalysis composition of claim 1, wherein a first mass percent of the first binder within the catalysis composition is between about 4% and about 8%, and wherein a second mass percent of the second binder within the catalysis composition is between about 4% and about 8%.

13. The catalysis composition of claim 1, wherein the support material comprises alumina.

14. The catalysis composition of claim 1, wherein a surface area of the catalysis composition is from about 160 $m^2/g$ to about 200 $m^2/g$.

15. The catalysis composition of claim 1, wherein the manganese oxide catalyst is impregnated in the support material such that at least about 15% of a total number of metal atoms in the catalysis composition are detectable by surface x-ray photoelectron spectroscopy (XPS).

16. The catalysis composition of claim 1, wherein a cumulative pore volume of the catalysis composition is from about 0.85 mL/g to about 2.0 mL/g.

17. The catalysis composition of claim 1, wherein the manganese oxide catalyst comprises manganese oxide crystallites.

18. The catalysis composition of claim 1, wherein the catalysis composition, when coated onto an automobile radiator, has a deactivation factor of at least 0.7, wherein the deactivation factor is the ratio of aged catalyst % ozone conversion to fresh catalyst % ozone conversion, wherein the aged % conversion is after exposure of the coated radiator to the equivalent of 150,000 miles driving time.

19. The catalysis composition of claim 1, wherein the support material is selected from a group consisting of alumina, silica, and combinations thereof.

20. The catalyst composition of claim 1, wherein at least 60% of the manganese oxide catalyst is in amorphous form.

21. The catalyst composition of claim 1, wherein at least 75% of the manganese oxide catalyst is in amorphous form.

22. The catalyst composition of claim 1, wherein at least 85% of the manganese oxide catalyst is in amorphous form.

23. A catalysis device comprising:
an automobile component; and
the catalysis composition of claim 1, wherein the catalysis composition is coated onto the automobile component.

24. A method of preparing a catalysis device of claim 23, comprising:
providing a slurry of the catalysis composition, and
coating the slurry onto the automobile component to produce a catalyst layer, wherein, after coating the slurry onto the component, an ultrasonic washcoat adhesion weight loss of the substrate is less than 1.60%, wherein
the weight loss is weight difference of the coated component after being immersed in deionized water and exposed to ultrasonic waves at 25 kHz and 500 Watts for 5 minutes and dried at 90° C.

25. The method of claim 24, wherein coating the slurry onto the component comprises drying the slurry at a temperature ranging from about 80° C. to about 120° C. to produce the catalyst layer.

26. The method of claim 24, wherein at least one of the first binder or the second binder is a styrene acrylic binder.

* * * * *